(12) United States Patent
Asanoi et al.

(10) Patent No.: US 11,567,315 B2
(45) Date of Patent: Jan. 31, 2023

(54) HEAD-UP DISPLAY DEVICE

(71) Applicant: NITTO DENKO CORPORATION, Ibaraki (JP)

(72) Inventors: Yoshiaki Asanoi, Ibaraki (JP); Takehito Fuchida, Ibaraki (JP); Katsunori Takada, Ibaraki (JP)

(73) Assignee: NITTO DENKO CORPORATION, Ibaraki (JP)

( * ) Notice: Subject to any disclaimer, the term of this patent is extended or adjusted under 35 U.S.C. 154(b) by 240 days.

(21) Appl. No.: 16/756,957

(22) PCT Filed: Oct. 16, 2018

(86) PCT No.: PCT/JP2018/038450
§ 371 (c)(1),
(2) Date: Apr. 17, 2020

(87) PCT Pub. No.: WO2019/093079
PCT Pub. Date: May 16, 2019

(65) Prior Publication Data
US 2021/0191119 A1      Jun. 24, 2021

(30) Foreign Application Priority Data

Nov. 9, 2017 (JP) .............................. JP2017-216115
Oct. 15, 2018 (JP) .............................. JP2018-194391

(51) Int. Cl.
*G02B 27/01* (2006.01)
*B60K 35/00* (2006.01)
(Continued)

(52) U.S. Cl.
CPC .......... *G02B 27/0101* (2013.01); *B60K 35/00* (2013.01); *C07C 245/10* (2013.01); *G02B 5/3083* (2013.01); *B60K 2370/1529* (2019.05)

(58) Field of Classification Search
CPC .... G02B 27/0101; G02B 5/3083; G02B 5/30; G02B 5/305; G02B 2027/0118;
(Continued)

(56) References Cited

U.S. PATENT DOCUMENTS

| 4,787,711 A | 11/1988 | Suzuki et al. |
| 4,892,386 A | 1/1990 | Suzuki et al. |

(Continued)

FOREIGN PATENT DOCUMENTS

| CN | 106030354 A | 10/2016 |
| CN | 106030354 A | * 10/2016 |

(Continued)

OTHER PUBLICATIONS

International Search Report dated Jan. 8, 2019, issued in counterpart International Application No. PCT/JP2018/038450 (2 pages).

(Continued)

*Primary Examiner* — Brent D Castiaux
(74) *Attorney, Agent, or Firm* — WHDA, LLP

(57) ABSTRACT

A head-up display apparatus includes: a display unit, which includes a display cell and a first polarizing plate with a retardation layer arranged on an output side of the display cell, the first polarizing plate with a retardation layer including a polarizer and a first retardation layer in the stated order from the display cell side, and which is configured to output projection light; at least one reflector configured to reflect the projection light; a housing, which has an opening portion, and which is configured to store the display unit and the reflector therein; a cover member configured to cover the opening portion; and a second polarizing plate with a retardation layer, which is arranged on a housing inner side of the cover member, and which includes a polarizer and a second retardation layer in the stated order from the cover member side.

4 Claims, 3 Drawing Sheets

(51) Int. Cl.
C07C 245/10 (2006.01)
G02B 5/30 (2006.01)

(58) Field of Classification Search
CPC ........... B60K 35/00; B60K 2370/1529; B60K 2370/693; B60K 37/04; C07C 245/10
See application file for complete search history.

(56) References Cited

U.S. PATENT DOCUMENTS

| | | | |
|---|---|---|---|
| 9,904,052 | B2 | 2/2018 | Matsuda et al. |
| 10,241,241 | B2 | 3/2019 | Tanaka et al. |
| 10,345,584 | B2 | 7/2019 | Yokota et al. |
| 10,495,877 | B2 | 12/2019 | Kuzuhara et al. |
| 10,656,415 | B2 | 5/2020 | Kuzuhara et al. |
| 2010/0277786 | A1* | 11/2010 | Anderson ............ G02F 1/1313 359/485.05 |
| 2013/0279016 | A1 | 10/2013 | Finger |
| 2016/0327788 | A1 | 11/2016 | Yamaoka |
| 2017/0045738 | A1 | 2/2017 | Kim et al. |
| 2017/0052370 | A1* | 2/2017 | Matsuda ................. G02B 1/08 |
| 2017/0235030 | A1 | 8/2017 | Tanaka et al. |
| 2017/0283700 | A1* | 10/2017 | Yoshioka ........... C09K 19/3823 |
| 2017/0299922 | A1 | 10/2017 | Matsuura et al. |
| 2018/0067311 | A1 | 3/2018 | Yokota et al. |
| 2018/0348515 | A1 | 12/2018 | Kuzuhara et al. |
| 2018/0356631 | A1* | 12/2018 | Kuzuhara ............ G02B 27/286 |

FOREIGN PATENT DOCUMENTS

| | | |
|---|---|---|
| CN | 106415335 A | 2/2017 |
| EP | 3153895 A1 | 4/2017 |
| EP | 3333615 A1 | 6/2018 |
| JP | 62-225429 A | 10/1987 |
| JP | 6-885 U | 1/1994 |
| JP | H11-281916 A | 10/1999 |
| JP | 2008-70504 A | 3/2008 |
| JP | 2010-152005 A | 7/2010 |
| JP | 2012-194357 A | 10/2012 |
| JP | 2014-044244 A | 3/2014 |
| JP | 2015-222337 A | 12/2015 |
| TW | 201643512 A | 12/2016 |
| TW | 201723585 A | 7/2017 |
| TW | 201727312 A | 8/2017 |
| WO | 2012/124400 A1 | 9/2012 |
| WO | 2016/047621 A1 | 3/2016 |
| WO | 2017/094248 A1 | 6/2017 |
| WO | 2017/094249 A1 | 6/2017 |
| WO | WO2017094248 A1 * | 6/2017 |

OTHER PUBLICATIONS

Office Action dated Oct. 15, 2021, issued in counterpart CN Application No. 201880067760.0 with English translation. (14 pages).

Extended European search report dated Jun. 11, 2021, issued in counterpart EP application No. 18876797.4. (8 pages).

Office Action dated Jun. 28, 2022 issued in counterpart TW application No. 107136912 with English translation. (12 pages).

Office Action dated Apr. 22, 2022, issued in counterpart CN Application No. 201880067760.0, with English machine translation. (14 pages).

* cited by examiner

HEAD-UP DISPLAY DEVICE

TECHNICAL FIELD

The present invention relates to a head-up display apparatus.

BACKGROUND ART

The driver of a vehicle performs driving while carefully viewing the front through a windshield, and visually observing meters on an instrument panel. That is, the line of sight of the driver moves toward the front and the meters below. When the driver can view the meters while viewing the front, the movement of the line of sight does not occur, and hence an improvement in drivability (finally safety) can be expected. In view of the finding, ahead-up display apparatus has started to be developed and put into practical use. In the head-up display apparatus, a cover member configured to cover the opening portion of an optical path is arranged for preventing the entry of foreign matter, such as dust, into a housing in which an optical system is stored. Further, a polarizing plate may be bonded to the cover member for preventing an increase in temperature in the housing (specifically for preventing the incidence of sunlight) (e.g., Patent Literature 1). A related-art head-up display apparatus has an insufficient commercial value because its concealability for the inside of its housing is insufficient, and hence the inside is seen. Meanwhile, when an attempt is made to improve the concealability of the head-up display apparatus, its display brightness reduces, and hence its viewability becomes insufficient.

CITATION LIST

Patent Literature

[PTL 1] JP 2008-70504 A

SUMMARY OF INVENTION

Technical Problem

The present invention has been made to solve the conventional problems, and an object of the present invention is to provide a head-up display apparatus capable of simultaneously satisfying concealability for its inside and display brightness.

Solution to Problem

A head-up display apparatus of the present invention includes: a display unit, which includes a display cell and a first polarizing plate with a retardation layer arranged on an output side of the display cell, the first polarizing plate with a retardation layer including a polarizer and a first retardation layer in the stated order from a display cell side, and which is configured to output projection light; at least one reflector configured to reflect the projection light; a housing, which has an opening portion, and which is configured to store the display unit and the reflector therein; a cover member configured to cover the opening portion; and a second polarizing plate with a retardation layer, which is arranged on a housing inner side of the cover member, and which includes a polarizer and a second retardation layer in the stated order from a cover member side. The first retardation layer and the second retardation layer each have an in-plane retardation Re(550) of from 100 nm to 200 nm.

In one embodiment, the polarizers each contain an aromatic disazo compound represented by the following formula (1):

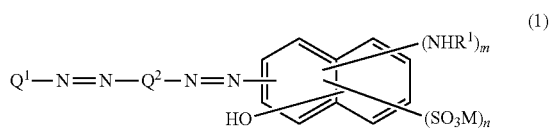

in the formula (1), $Q^1$ represents a substituted or unsubstituted aryl group, $Q^2$ represents a substituted or unsubstituted arylene group, $R^1$s each independently represent a hydrogen atom, a substituted or unsubstituted alkyl group, a substituted or unsubstituted acetyl group, a substituted or unsubstituted benzoyl group, or a substituted or unsubstituted phenyl group, M represents a counterion, "m" represents an integer of from 0 to 2, and "n" represents an integer of from 0 to 6, provided that at least one of "m" or "n" does not represent 0, a relationship of $1 \leq m+n \leq 6$ is satisfied, and when "m" represents 2, the respective $R^1$s may be identical to or different from each other.

In one embodiment, the polarizers each have a thickness of from 100 nm to 1,000 nm.

In one embodiment, the head-up display apparatus is configured so that an angle of reflection of the projection light output from the housing through the opening portion with respect to a windshield is from 10° to 50°.

Advantageous Effects of Invention

According to the embodiment of the present invention, in the head-up display apparatus, the first polarizing plate with a retardation layer having the following feature is laminated on the output side of the display cell: the first polarizing plate with a retardation layer includes the polarizer and the first retardation layer in the stated order from the display cell side of the display unit. In addition, the second polarizing plate with a retardation layer having the following feature is laminated on the housing inner side of the cover member configured to cover the opening portion of the housing: the second polarizing plate with a retardation layer includes the polarizer and the second retardation layer in the stated order from the cover member side. Accordingly, the head-up display apparatus capable of simultaneously satisfying concealability for its inside and display brightness can be achieved.

DESCRIPTION OF EMBODIMENTS

Now, embodiments of the present invention are described. However, the present invention is not limited to these embodiments.

A. Overall Configuration of Head-Up Display Apparatus

Figure 1:
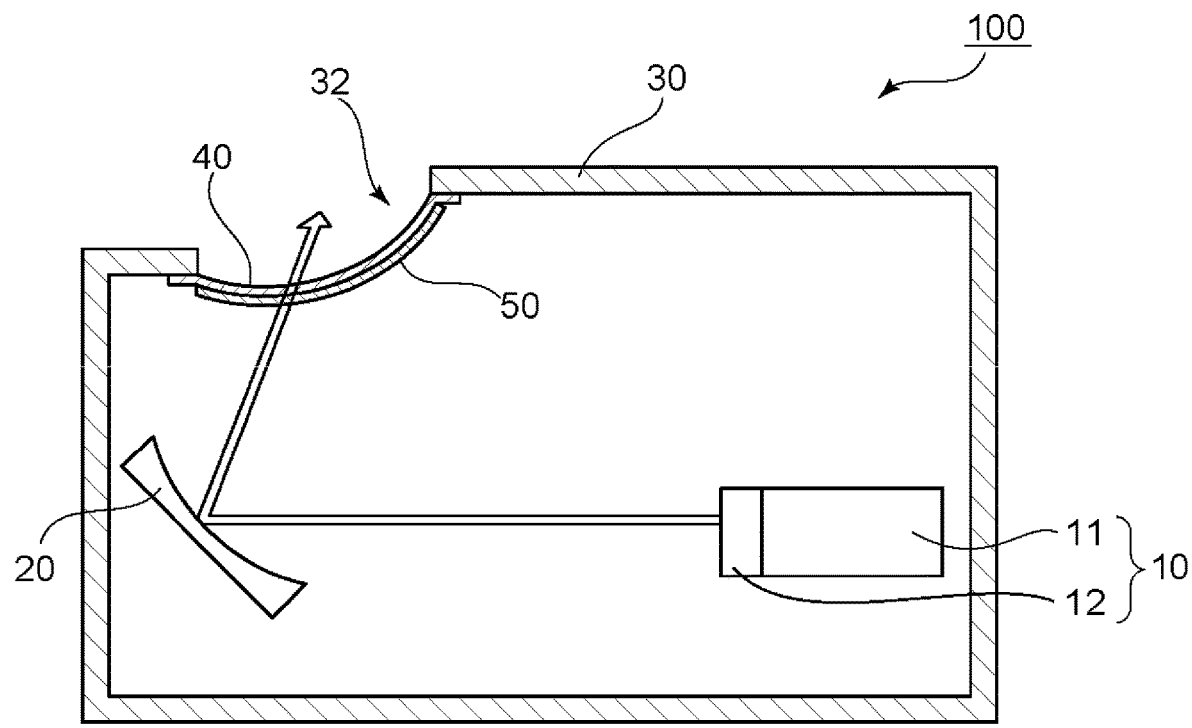
FIG. 1 is a schematic partial sectional view for illustrating a head-up display apparatus according to one embodiment of the present invention.
Figure 2:
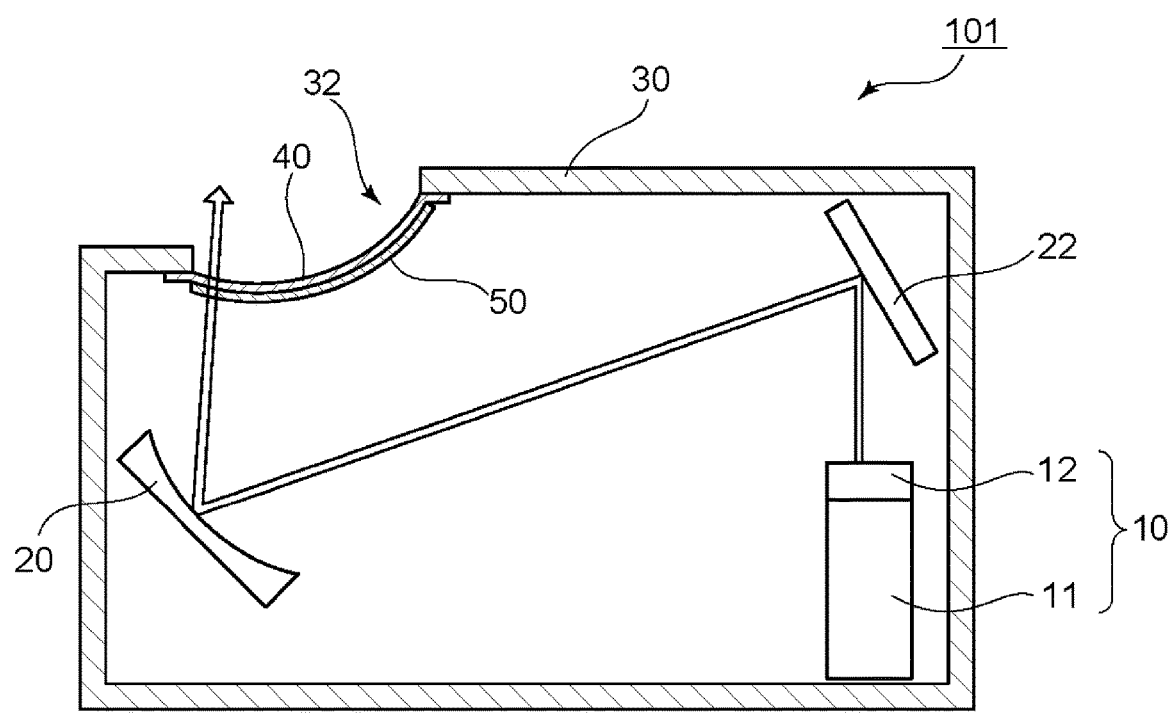
FIG. 2 is a schematic partial sectional view for illustrating a head-up display apparatus according to another embodiment of the present invention.

FIG. 1 is a schematic partial sectional view for illustrating a head-up display apparatus according to one embodiment of the present invention. A head-up display apparatus 100 includes: a display unit 10, which includes a display cell 11 and a first polarizing plate 12 with a retardation layer, and which is configured to output projection light; at least one reflector (in the illustrated example, one reflector) 20 configured to reflect the projection light; a housing 30, which has an opening portion 32, and which is configured to store the display unit 10 and the reflector 20 therein; a cover member 40 configured to cover the opening portion 32; and a second polarizing plate 50 with a retardation layer, which is arranged on the housing inner side of the cover member 40. Although the one reflector 20 is arranged in the embodiment of FIG. 1, two reflectors 20 and 22 may be arranged like a head-up display apparatus 101 illustrated in FIG. 2.

Any appropriate configuration may be adopted as the display unit 10. The display unit is typically, for example, a liquid crystal display apparatus. Therefore, the display cell 11 is, for example, a liquid crystal cell. Any appropriate configuration may be adopted as the configuration (e.g., driving mode) of the liquid crystal cell.

Figure 3:
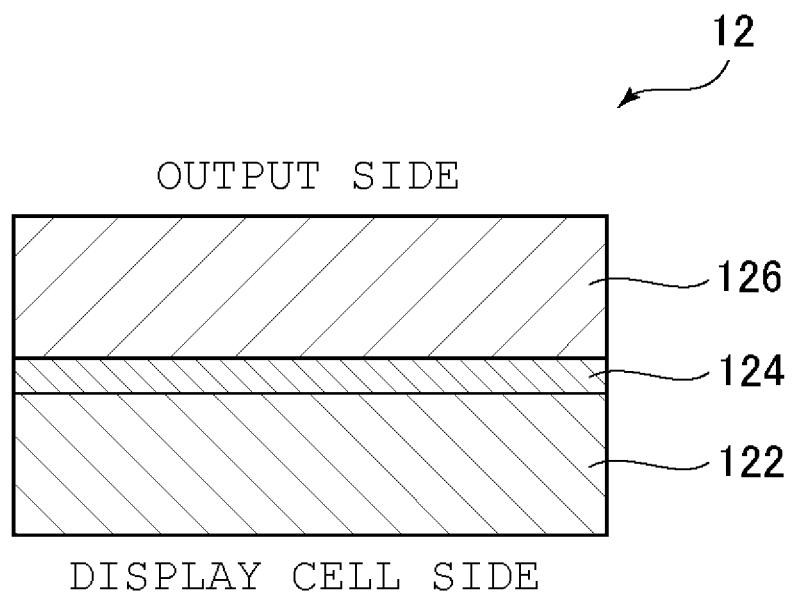
FIG. 3 is a schematic sectional view for illustrating an example of a first polarizing plate with a retardation layer that may be used in the head-up display apparatus of the present invention.

In the embodiment of the present invention, as described above, the display unit 10 includes the display cell 11 and the first polarizing plate 12 with a retardation layer. The first polarizing plate 12 with a retardation layer is typically bonded to the output side of the display cell 11 via a pressure-sensitive adhesive. As illustrated in FIG. 3, the first polarizing plate 12 with a retardation layer includes a polarizer 124 and a first retardation layer 126 in the stated order from the display cell 11 side. The first polarizing plate 12 with a retardation layer may include a substrate 122 on the display cell 11 side of the polarizer 124 as required like the illustrated example. In the embodiment of the present invention, the first retardation layer 126 has an in-plane retardation Re(550) of from 100 nm to 200 nm. When the in-plane retardation of the first retardation layer falls within such range, the setting of an angle formed between the slow axis of the first retardation layer and the absorption axis of the polarizer to a predetermined angle (described later) imparts, to the layer, a function of converting the light output from the display unit into circularly polarized light or elliptically polarized light. Such output light (circularly polarized light or elliptically polarized light) is converted into linearly polarized light by the second retardation layer of the second polarizing plate with a retardation layer to be described later, and is discharged from the opening portion to the outside of the housing. Details of the first polarizing plate with a retardation layer are described later in the section C together with the second polarizing plate with a retardation layer. The term "Re(λ)" as used herein refers to the in-plane retardation of a film measured at 23° C. with light having a wavelength of A nm. Therefore, the term "Re(550)" refers to the in-plane retardation of the film measured at 23° C. with light having a wavelength of 550 nm. When the thickness of the film is represented by d (nm), the Re(λ) is determined from the expression "Re=(nx−ny)× d" where "nx" represents a refractive index in the direction in which a refractive index in the plane of the film becomes maximum (that is, a slow axis direction), and "ny" represents a refractive index in the direction perpendicular to the slow axis in the plane (that is, a fast axis direction).

Any appropriate configuration may be adopted as the reflector 20 (and, if present, the reflector 22). The reflector 20 has, for example, a mirror portion and a mirror holder configured to hold the mirror portion at a predetermined position in the housing 30. The mirror portion may be a plane mirror, or may be a concave mirror. In the illustrated example, the concave mirror is adopted. The use of the concave mirror enables enlarged display of a video to be projected. The radius of curvature of the concave mirror may be appropriately set in accordance with, for example, a purpose and the size of the video to be projected. When the reflector 22 is arranged, the reflector 22 may be, for example, a plane mirror (cold mirror) configured to transmit only an infrared ray and to reflect a visible ray and UV light.

The housing 30 is a box-shaped member having an internal space capable of storing the display unit 10 and the reflectors 20 and 22. The housing 30 typically has the opening portion 32, and the projection light output from the display unit 10 through the opening portion 32 is discharged to the outside of the housing 30. The housing 30 may include any appropriate material. A preferred constituent material therefor is, for example, a material that hardly undergoes a temperature increase due to irradiation with sunlight, and that is easy to form. Specific examples of such material include an acrylic resin, an epoxy-based resin, a polyester-based resin, a urethane-based resin, a polyolefin-based resin, a fluorine-based resin, and a phenoxy-based resin. The housing 30 may be incorporated in a part of an automobile, or may be a member independent of an automobile. For example, a dashboard of an automobile may be used as the housing.

The cover member 40 is a plate-shaped member configured to cover the opening portion 32 of the housing 30 so that dust does not enter the inside of the housing 30. The cover member 40 is typically transparent, and the projection light reflected from the reflector 20 passes the cover member 40 to be discharged to the outside of the housing 30. Details of the cover member are described later in the section B.

Figure 4:
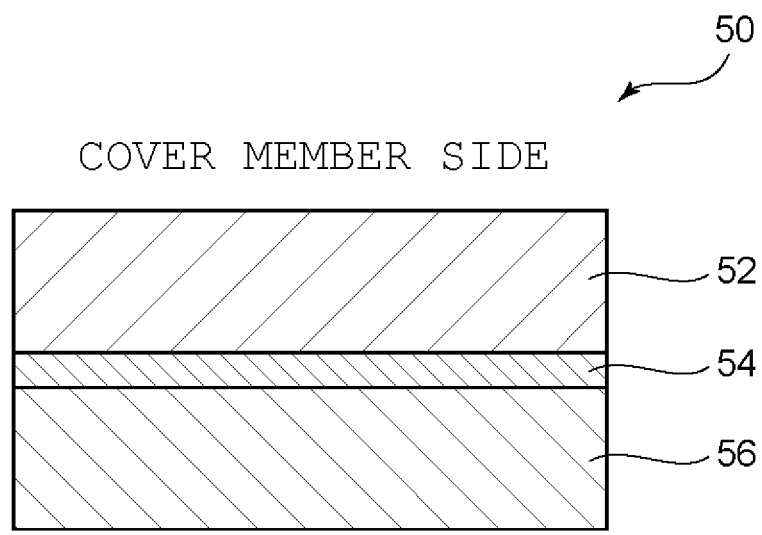
FIG. 4 is a schematic sectional view for illustrating an example of a second polarizing plate with a retardation layer that may be used in the head-up display apparatus of the present invention.

In the embodiment of the present invention, the second polarizing plate 50 with a retardation layer is bonded to the housing inner side of the cover member 40 via a pressure-sensitive adhesive. As illustrated in FIG. 4, the second polarizing plate 50 with a retardation layer includes a polarizer 54 and a second retardation layer 56 in the stated order from the cover member 40 side. The second polarizing plate 50 with a retardation layer may include a substrate 52 on the cover member 40 side of the polarizer 54 as required like the illustrated example. In the embodiment of the present invention, the second retardation layer 56 has an in-plane retardation Re(550) of from 100 nm to 200 nm. When the in-plane retardation of the second retardation layer falls within such range, the setting of an angle formed between the slow axis of the second retardation layer and the absorption axis of the polarizer to a predetermined angle (described later: further particularly preferably around 45°) imparts, to the layer, a function of converting linearly polarized light into circularly polarized light or elliptically polarized light, or a function of converting circularly polarized light or elliptically polarized light into linearly polarized light. As a result, the projection light (circularly polarized light or elliptically polarized light) output from the display unit (liquid crystal display apparatus) can be satisfactorily converted into linearly polarized light and discharged to the outside of the housing 30. Further, natural light from the outside is converted into circularly polarized light or elliptically polarized light by the second retardation layer, and when the circularly polarized light or the elliptically polarized light is reflected in the housing, its rotation direction is reversed. Such circularly polarized light or elliptically polarized light that has been reflected (whose rotation direction has been reversed) is absorbed by the second retardation layer, and hence its discharge to the outside of the housing can be substantially prevented. As a result, the brightness of the projection light from the display unit to be discharged to the outside of the housing can be maintained at a high level, and the viewability of the inside of the housing can be markedly reduced (i.e., concealability for the inside of the housing can be made extremely excellent). In other words, a head-up display apparatus capable of simultaneously satisfying concealability for its inside and display brightness can be achieved by incorporating each of the first polarizing plate with a retardation layer (the first retardation layer) and the second polarizing plate with a retardation layer (the second retardation layer) into a predetermined position of the head-up display apparatus under a predetermined state. Further, when the second polarizing plate with a retardation layer is arranged, the incidence (passing) of the sunlight can be suppressed by the polarizer of the second polarizing plate with a retardation layer. Accordingly, the heat resistance of the head-up display apparatus can be improved. Details of the second polarizing plate with a retardation layer are described later in the section C together with the first polarizing plate with a retardation layer.

In the embodiment of the present invention, the first polarizing plate with a retardation layer and the second polarizing plate with a retardation layer are typically arranged so that the absorption axes of their respective polarizers are substantially parallel to each other. Further, the first polarizing plate with a retardation layer and the second polarizing plate with a retardation layer are typically arranged so that the slow axes of their respective retardation layers are substantially perpendicular to each other. When the first polarizing plate with a retardation layer and the second polarizing plate with a retardation layer are arranged so as to form such axial angles, the functions of mutually converting linearly polarized light and circularly polarized light or elliptically polarized light exhibited by the two polarizing plates with retardation layers can be made sufficient. The expressions "substantially parallel" and "approximately parallel" as used herein each include a case in which an angle formed between two directions is 0°±7°, and the angle is preferably 0°±5°, more preferably 0°±3°. The expressions "substantially perpendicular" and "approximately perpendicular" as used herein each include a case in which an angle formed between two directions is 90°±7°, and the angle is preferably 90°±5°, more preferably 90°±3°. Further, the simple expression "perpendicular" or "parallel" as used herein may include a state in which two directions are substantially perpendicular, or substantially parallel, to each other.

Figure 5:
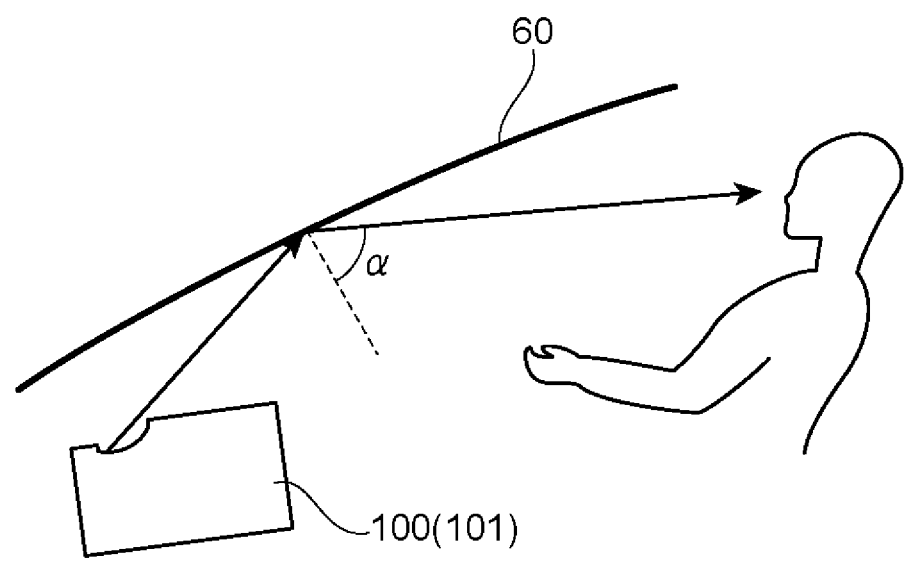
FIG. 5 is a schematic view for illustrating a relationship between projection light in the head-up display apparatus of the present invention and a windshield.

In one embodiment, as illustrated in FIG. 5, the head-up display apparatus is configured so that the angle of reflection a of the projection light output from the housing 30 through the opening portion 32 with respect to a windshield 60 is from 10° to 50°. With such configuration, a head-up display apparatus having more excellent concealability for its inside and more excellent display brightness can be achieved by a synergistic effect with the effects of the first and second polarizing plates with retardation layers described above. The angle of reflection a is preferably from 15° to 45°, more preferably from 20° to 40°. The angle of reflection a can be controlled by adjusting the angle of the reflector 20. Specifically, the mirror holder only needs to be configured so that its angle can be adjusted. The mirror holder has, for example, a shaft whose peripheral surface is connected to the rear surface of the mirror portion, and a controlling portion connected to an end portion of the shaft. The angle of the mirror portion changes following the rotation of the shaft, and hence the angle of the mirror portion can be indirectly adjusted through the control of the rotation of the shaft by the controlling portion. The angle of the mirror portion may typically be adjusted in accordance with the shape of the windshield.

A detailed description of the detailed configuration of the head-up display apparatus is omitted because any appropriate configuration commonly used in the art is adopted. The cover member and the polarizing plate with a retardation layer are specifically described below.

B. Cover Member

As described above, the cover member 40 is typically transparent. The term "transparent" as used herein means that the member has a property of transmitting visible light having a wavelength of from 360 nm to 830 nm. The term "transparent" includes: a case in which the member is substantially free from absorbing visible light, and transmits light having any wavelength in a visible light region (colorless transparent); and a case in which the member absorbs light beams having some wavelengths in the visible light region, and transmits light having a wavelength except the wavelengths (colored transparent). The cover member 40 is preferably colorless transparent. The total light transmittance of the cover member is preferably 50% or more, more preferably 70% or more, still more preferably 90% or more. The total light transmittance is a value measured in conformity with JIS K 7375.

The surface shape of the cover member may be appropriately set in accordance with the shape of the opening portion 32. For example, the portion of the cover member configured to cover the opening portion may include only a flat surface or only a curved surface, or the portion configured to cover the opening portion may include a plurality of flat surfaces and/or a plurality of curved surfaces. The surface shape of the cover member typically includes only a flat surface or only a curved surface. In the illustrated example, a cover member whose portion configured to cover the opening portion includes only a curved surface is used.

The thickness of the cover member may be, for example, from 10 μm to 1,000 μm. When the cover member is excessively thick, there is a risk in that the transmittance of the projection light reduces (the light loss of the projection light increases), and moreover, the reduction serves as a cause for the occurrence of a double image. When the cover member is excessively thin, there is a risk in that its mechanical strength becomes insufficient, and hence its covering function becomes insufficient.

The cover member may include any appropriate transparent material. Typical examples thereof include a resin and glass. Specific examples of the resin include: ester-based resins, such as polyethylene terephthalate and polyethylene naphthalate; cellulose-based resins, such as diacetyl cellulose and triacetyl cellulose; polycarbonate-based resins, such as bisphenol A-based polycarbonate; acrylic resins, such as polymethyl methacrylate; acrylic resins, such as a lactone-modified acrylic resin; styrene-based resins, such as polystyrene and an acrylonitrile-styrene copolymer; olefin-based resins, such as polyethylene, polypropylene, a polyolefin having a cyclic structure or a norbornene structure, and an ethylene-propylene copolymer; vinyl chloride-based resins; amide-based resins, such as aromatic polyamide; imide-based resins; sulfone-based resins; polyether sulfone-based resins; polyether ether ketone-based resins; polyphenylene sulfide-based resins; vinyl alcohol-based resins; vinylidene chloride-based resins; vinyl butyral-based resins; arylate-based resins; polyoxymethylene-based resins; and epoxy-based resins. Those resins may be used alone or in combination thereof.

C. First Polarizing Plate with Retardation Layer and Second Polarizing Plate with Retardation Layer Similar descriptions are applied to the respective constituents of the first polarizing plate with a retardation layer and the second polarizing plate with a retardation layer (typically the polarizers 124 and 54, the first retardation layer 126 and the second retardation layer 56, and the substrates 122 and 52), and hence the constituents are collectively described except for the case where the constituents need to be separately described. For example, the polarizers 124 and 54 may be identical to or different from each other. The same holds true for the first retardation layer 126 and the second retardation layer 56, and the substrates 122 and 52.

C-1. Polarizer

Any appropriate polarizer may be adopted as the polarizer. Typical examples thereof include an iodine-based polarizer and a lyotropic liquid crystal polarizer.

A resin film for forming the iodine-based polarizer may be a single-layer resin film, or may be produced by using a laminate of two or more layers.

Specific examples of the polarizer formed of a single-layer resin film include: a polarizer obtained by subjecting a hydrophilic polymer film, such as a polyvinyl alcohol (PVA)-based resin film, a partially formalized PVA-based resin film, or an ethylene-vinyl acetate copolymer-based partially saponified film, to dyeing treatment with a dichroic substance, such as iodine or a dichroic dye, and stretching treatment; and a polyene-based alignment film, such as a dehydration-treated product of PVA or a dehydrochlorination-treated product of polyvinyl chloride. A polarizer obtained by dyeing the PVA-based resin film with iodine and uniaxially stretching the resultant is preferably used because the polarizer is excellent in optical characteristics.

The dyeing with iodine is performed by, for example, immersing the PVA-based resin film in an aqueous solution of iodine. The stretching ratio of the uniaxial stretching is preferably from 3 times to 7 times. The stretching may be performed after the dyeing treatment, or may be performed while the dyeing is performed. In addition, the dyeing may be performed after the stretching has been performed. The PVA-based resin film is subjected to swelling treatment, cross-linking treatment, washing treatment, drying treatment, or the like as required. For example, when the PVA-based resin film is immersed in water to be washed with water before the dyeing, contamination or an antiblocking agent on the surface of the PVA-based resin film can be washed off. In addition, the PVA-based resin film is swollen and hence dyeing unevenness or the like can be prevented.

A specific example of the polarizer obtained by using a laminate is a polarizer obtained by using a laminate of a resin substrate and a PVA-based resin layer (PVA-based resin film) laminated on the resin substrate or a laminate of a resin substrate and a PVA-based resin layer formed on the resin substrate through application. The polarizer obtained by using the laminate of the resin substrate and the PVA-based resin layer formed on the resin substrate through application may be produced, for example, by: applying a PVA-based resin solution to the resin substrate; drying the solution to form the PVA-based resin layer on the resin substrate, to thereby provide the laminate of the resin substrate and the PVA-based resin layer; and stretching and dyeing the laminate to turn the PVA-based resin layer into the polarizer. In this embodiment, the stretching typically includes stretching of the laminate under a state in which the laminate is immersed in an aqueous solution of boric acid. Further, the stretching may further include in-air stretching of the laminate at high temperature (e.g., 95° C. or more) before the stretching in the aqueous solution of boric acid as required. The resultant laminate of the resin substrate and the polarizer may be used as it is (i.e., the resin substrate may be used as a protective layer for the polarizer). Alternatively, a product obtained as described below may be used: the resin substrate is peeled from the laminate of the resin substrate and the polarizer, and any appropriate protective layer in accordance with purposes is laminated on the peeling surface. Details of such method of producing the polarizer are described in, for example, JP 2012-73580 A, the description of which is incorporated herein by reference in its entirety.

The lyotropic liquid crystal polarizer is excellent in heat resistance, and hence can result in a further improvement in heat resistance of the head-up display apparatus. The lyotropic liquid crystal polarizer contains, for example, an aromatic disazo compound represented by the following formula (1):

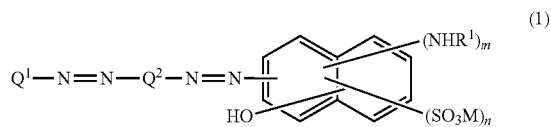

(1)

in the formula (1), $Q^1$ represents a substituted or unsubstituted aryl group, $Q^2$ represents a substituted or unsubstituted arylene group, $R^1$s each independently represent a hydrogen atom, a substituted or unsubstituted alkyl group, a substituted or unsubstituted acetyl group, a substituted or unsubstituted benzoyl group, or a substituted or unsubstituted phenyl group, M represents a counterion, "m" represents an integer of from 0 to 2, and "n" represents an integer of from 0 to 6, provided that at least one of "m" or "n" does not represent 0, a relationship of $1 \leq m+n \leq 6$ is satisfied, and when "m" represents 2, the respective $R^1$s may be identical to or different from each other.

OH, $(NHR^1)_m$, and $(SO_3M)_n$ represented in the formula (1) may each be bonded to any one of the seven substitution sites of a naphthyl ring.

The position at which the naphthyl group and azo group (—N═N—) of the formula (1) are bonded to each other is not particularly limited. The azo group is preferably bonded to the 1-position or 2-position of the naphthyl group.

When the alkyl group, the acetyl group, the benzoyl group, or the phenyl group represented by $R^1$ of the formula (1) has a substituent, examples of the substituent include substituents given as examples of a substituent in the following aryl group or arylene group. $R^1$ represents preferably a hydrogen atom, a substituted or unsubstituted alkyl group, or a substituted or unsubstituted acetyl group, more preferably a hydrogen atom. The substituted or unsubstituted alkyl group is, for example, a substituted or unsubstituted alkyl group having 1 to 6 carbon atoms.

Preferred examples of M (the counterion) of the formula (1) include: a hydrogen ion; an ion of an alkali metal, such as Li, Na, K, or Cs; an ion of an alkaline earth metal, such as Ca, Sr, or Ba; any other metal ion; an ammonium ion that may be substituted with an alkyl group or a hydroxyalkyl group; and a salt of an organic amine. Examples of the metal ion include $Ni^+$, $Fe^{3+}$, $Cu^{2+}$, $Ag^+$, $Zn^{2+}$, $Al^{3+}$, $Pd^{2+}$, $Cd^{2+}$, $Sn^{2+}$, $Co^{2+}$, $Mn^{2+}$, and $Ce^{3+}$. Examples of the organic amine include: an alkylamine having 1 to 6 carbon atoms; an alkylamine that has 1 to 6 carbon atoms and has a hydroxyl group; and an alkylamine that has 1 to 6 carbon atoms and has a carboxyl group. When two or more $SO_3Ms$ are present in the formula (1), the respective Ms may be identical to or different from each other. In addition, when M of $SO_3M$ in the formula (1) represents a cation that is divalent or more, the cat ion may be bonded to $SO_3^-$ of any other adjacent azo-based compound molecule to form a supramolecular associate.

"m" of the formula (1) preferably represents 1. In addition, "n" of the formula (1) preferably represents 1 or 2.

Specific examples of the naphthyl group of the formula (1) include groups represented by the formula (a) to the formula (1) below. $R^1$s and Ms of the formula (a) to the formula (1) are as described for the formula (1).

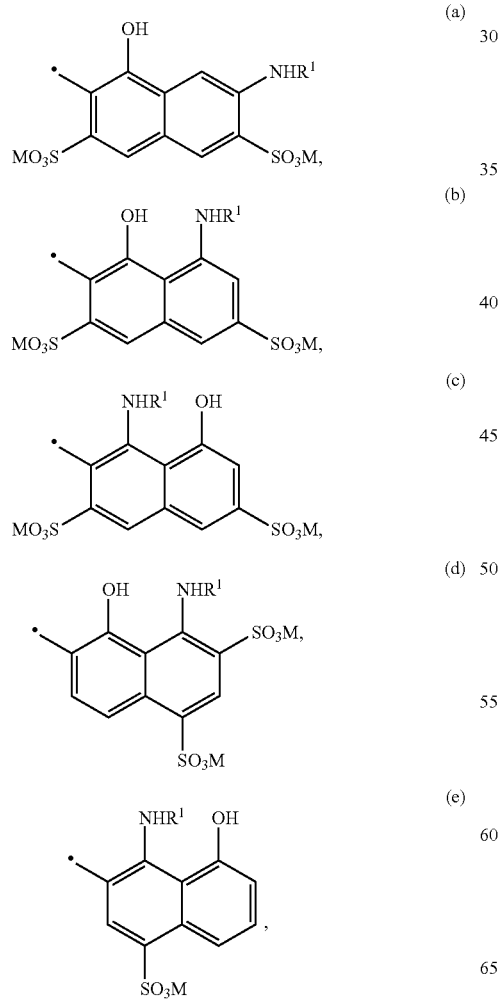

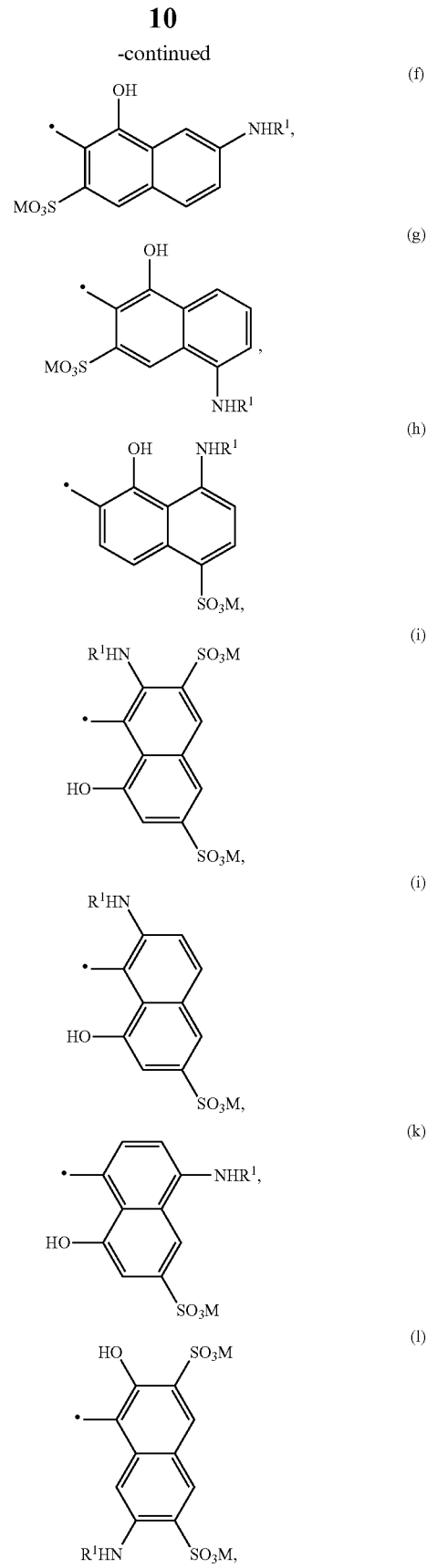

The aryl group represented by $Q^1$ in the formula (1) is, for example, a fused ring group in which two or more benzene rings are fused to each other, such as a naphthyl group, as well as a phenyl group. The arylene group represented by $Q^2$ is, for example, a fused ring group in which two or more benzene rings are fused to each other, such as a naphthylene group, as well as a phenylene group.

The aryl group represented by $Q^1$ or the arylene group represented by $Q^2$ may have a substituent, or may be free of any substituent. Irrespective of whether the aryl group or the arylene group is substituted or unsubstituted, the aromatic disazo compound represented by the formula (1), which has a polar group, is excellent in solubility in an aqueous solvent.

When the aryl group or the aryl ene group has a substituent, examples of the substituent include: an alkyl group having 1 to 6 carbon atoms; an alkoxy group having 1 to 6 carbon atoms; an alkylamino group having 1 to 6 carbon atoms; a phenylamino group; an acylamino group having 1 to 6 carbon atoms; a hydroxyalkyl group having 1 to 6 carbon atoms, such as a dihydroxypropyl group; a carboxyl group, such as a COOM group; a sulfonic acid group, such as an $SO_3M$ group; a hydroxyl group; a cyano group; a nitro group; an amino group; and a halogeno group. The substituent is preferably one selected from an alkoxy group having 1 to 6 carbon atoms, a hydroxyalkyl group having 1 to 6 carbon atoms, a carboxyl group, a sulfonic acid group, and a nitro group. The aromatic disazo compound having any such substituent is particularly excellent in water solubility. The aryl group or the arylene group may be substituted with one kind of those substituents, or may be substituted with two or more kinds thereof. In addition, the aryl group or the arylene group may be substituted with the substituent at any ratio.

$Q^1$ of the formula (1) represents preferably a substituted or unsubstituted phenyl group, more preferably a phenyl group having the above-mentioned substituent. $Q^2$ of the formula represents preferably a substituted or unsubstituted naphthylene group, more preferably a naphthylene group having the above-mentioned substituent, particularly preferably a 1,4-naphthylene group having the above-mentioned substituent.

An aromatic disazo compound in which $Q^1$ of the formula (1) represents a substituted or unsubstituted phenyl group, and $Q^2$ thereof represents a substituted or unsubstituted 1,4-naphthylene group is represented by the following formula (2).

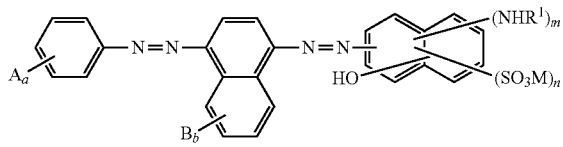

(2)

In the formula (2), $R^1$, M, "m", and "n" are as described for the formula (1). In the formula (2), A and B represent substituents, and "a" and "b" represent their numbers of substitutions. A and B each independently represent an alkyl group having 1 to 6 carbon atoms, an alkoxy group having 1 to 6 carbon atoms, an alkylamino group having 1 to 6 carbon atoms, a phenylamino group, an acylamino group having 1 to 6 carbon atoms, a hydroxyalkyl group having 1 to 6 carbon atoms, such as a dihydroxypropyl group, a carboxyl group, such as a COOM group, a sulfonic acid group, such as an $SO_3M$ group, a hydroxyl group, a cyano group, a nitro group, an amino group, or a halogeno group. "a" represents an integer of from 0 to 5, and "b" represents an integer of from 0 to 4, provided that at least one of "a" or "b" does not represent 0. When "a" represents 2 or more, the substituents A may be identical to or different from each other. When "b" represents 2 or more, the substituents B may be identical to or different from each other.

Of the aromatic disazo compounds included in the formula (2), an aromatic disazo compound represented by the following formula (3) is preferred. In the aromatic disazo compound represented by the formula (3), the substituent A is bonded to a para position with respect to an azo group (—N=N—). Further, the OH group of the naphthyl group of the aromatic disazo compound represented by the formula (3) is bonded to a position (ortho position) adjacent to an azo group. The use of such aromatic disazo compound represented by the formula (3) enables easy formation of a polarizer that is hardly shrunk by heating.

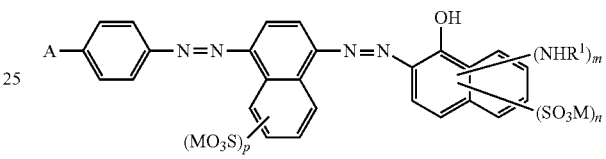

(3)

In the formula (3), $R^1$, M, "m", and "n" are as described for the formula (1), and A is as described for the formula (2). In the formula (3), "p" represents an integer of from 0 to 4. "p" represents preferably 1 or 2, more preferably 1.

The aromatic disazo compounds represented by the formulae (1) to (3) may each be synthesized in accordance with, for example, "Theoretical Production Dye Chemistry (Fifth Edition)" written by Yutaka Hosoda (published by Gihodo on Jul. 15, 1968, p. 135 to 152). For example, the aromatic disazo compound represented by the formula (3) may be synthesized by: subjecting an aniline derivative and a naphthalenesulfonic acid derivative to diazotization and a coupling reaction to provide a monoazo compound; then diazotizing the monoazo compound; and subjecting the resultant to a coupling reaction with a 1-amino-8-naphthol-sulfonic acid derivative.

The lyotropic liquid crystal polarizer may be produced by, for example, a method including a step B and a step C described below. As required, a step A may be performed before the step B, and a step D may be performed after the step C:

Step A: a step of subjecting the surface of a substrate to alignment treatment;

Step B: a step of applying a coating liquid containing the aromatic disazo compound represented by the formula (1) to the surface of the substrate to form a coating film;

Step C: a step of drying the coating film to form a polarizer that is a dried coating film; and Step D: a step of subjecting the surface of the polarizer obtained in the step C to water-resistant treatment.

(Step A)

The step A is a step of subjecting the surface of the substrate to the alignment treatment to impart an alignment-regulating force to the surface of the substrate. When a substrate having the alignment-regulating force in advance is used, there is no need to perform the step A. A method of imparting the alignment-regulating force is, for example, (a) a method including subjecting the surface of the substrate to rubbing treatment, (b) a method including forming a film of polyimide or the like on the surface of the substrate, and subjecting the surface of the formed film to rubbing treatment to form an alignment film, or (c) a method including forming a film formed of a photoreactive compound on the surface of the substrate, and irradiating the formed film with light to form an alignment film. When any one of the methods (b) and (c) is used, a polarizing plate with a retardation layer having the alignment film between its substrate and polarizer is produced. The substrate may be used as it is (in this case, the substrate may function as a protective layer for the polarizer), or the following may be performed: the substrate is peeled, and any appropriate protective film is arranged on the peeling surface.

(Step B)

The step B is a step of forming the coating film through the use of the coating liquid. The coating liquid contains the aromatic disazo compound and a solvent in which the aromatic disazo compound is dissolved or dispersed. The coating liquid is obtained by dissolving or dispersing the aromatic disazo compound in the solvent. As required, for example, any other polymer except the aromatic disazo compound and/or an additive may be added to the solvent.

Any appropriate solvent may be used as the solvent in which the aromatic disazo compound is dissolved or dispersed. An aqueous solvent is preferred. Examples of the aqueous solvent include water, a hydrophilic solvent, and a mixed solvent of water and the hydrophilic solvent. The hydrophilic solvent is a solvent that dissolves in water in an approximately uniform manner. Examples of the hydrophilic solvent include: alcohols, such as methanol and isopropyl alcohol; glycols, such as ethylene glycol; cellosolves, such as methyl cellosolve and ethyl cellosolve; ketones, such as acetone and methyl ethyl ketone; and esters, such as ethyl acetate. As the aqueous solvent, water or a mixed solvent of water and a hydrophilic solvent is preferably used.

The aromatic disazo compound represented by the formula (1) is an organic compound having lyotropic liquid crystallinity. Accordingly, when the temperature of the coating liquid, the concentration of the aromatic disazo compound therein, or the like is changed, the liquid shows a lyotropic liquid crystal phase. The lyotropic liquid crystal phase is produced by the formation of a supramolecular associate by the aromatic disazo compound in the liquid. The lyotropic liquid crystal phase may be confirmed and identified by an optical pattern observed with a polarizing microscope. The supramolecular associate is one large composite formed by the bonding of a plurality of aromatic disazo compound molecules through a hydrogen bond or the like.

The concentration of the aromatic disazo compound in the coating liquid is preferably adjusted so that the liquid shows a liquid crystal phase. The concentration of the aromatic disazo compound in the coating liquid is typically from 0.05 wt % to 50 wt %, preferably from 0.5 wt % to 40 wt %, more preferably from 1 wt % to 10 wt %. In addition, the pH of the coating liquid is adjusted to an appropriate value. The pH of the coating liquid is preferably from about 2 to about 10, more preferably from about 6 to about 8. Further, the temperature of the coating liquid is adjusted to preferably from 10° C. to 40° C., more preferably from 15° C. to 30° C.

The application of the coating liquid onto the substrate results in the formation of the coating film. In the coating film, the aromatic disazo compound is aligned in a predetermined direction by the alignment-regulating force of the substrate. An application method including using any appropriate coater may be adopted as a method of applying the coating liquid. Examples of the coater include a bar coater, a roll coater, a spin coater, a comma coater, a gravure coater, an air knife coater, and a die coater.

(Step C)

The step C is a step of forming the polarizer that is a dried coating film. The formation of the polarizer that is a dried coating film on the substrate provides a polarizing plate including the substrate and the polarizer.

When the coating film obtained in the step B is dried, the solvent in the coating film volatilizes, and hence a dried coating film (lyotropic liquid crystal polarizer) containing the aromatic disazo compound that is solid is formed. In the polarizer, the alignment of the aromatic disazo compound is fixed while the compound forms the supramolecular associate. A method of drying the coating film is, for example, natural drying or forced drying. Examples of the forced drying include drying under reduced pressure, heat drying, and heat drying under reduced pressure. The natural drying is preferably used. The drying time of the coating film may be appropriately set in accordance with the drying temperature thereof and the kind of the solvent. In the case of, for example, the natural drying, the drying time is preferably from 1 second to 120 minutes, more preferably from 10 seconds to 5 minutes. The drying temperature is preferably from 10° C. to 100° C., more preferably from 10° C. to 90° C., particularly preferably from 10° C. to 80° C. The drying temperature means not the temperature of the surface or inside of the coating film but the temperature of the atmosphere under which the coating film is dried.

(Step D)

The step D is a step of bringing a water-resistant treatment liquid into contact with the polarizer to impart water resistance to the polarizer. Any appropriate method may be adopted as a method of bringing the polarizer into contact with the water-resistant treatment liquid. Examples of the contact method include methods such as (a) the application of the water-resistant treatment liquid to the surface of the polarizer, (b) the immersion of the polarizing plate (polarizer) in a bath filled with the water-resistant treatment liquid, and (c) the passing of the polarizing plate (polarizer) through a bath filled with the water-resistant treatment liquid. The application of the water-resistant treatment liquid described in the (a) may be performed with, for example, any appropriate coater or spray.

Any appropriate liquid may be used as the water-resistant treatment liquid. The water-resistant treatment liquid contains, for example, a cross-linking agent having a function of cross-linking an organic dye and a solvent in which the cross-linking agent is dissolved or dispersed. The cross-linking agent may be, for example, an organic nitrogen compound, and the solvent may be, for example, an aqueous solvent. For example, an acyclic organic nitrogen compound having two or more cationic groups (preferably cationic groups each containing a nitrogen atom) in a molecule thereof is used as the organic nitrogen compound. Examples of the acyclic organic nitrogen compound (acyclic aliphatic nitrogen compound) include: an aliphatic diamine, such as an alkylene diamine, or a salt thereof; an aliphatic triamine, such as an alkylene triamine, or a salt thereof; an aliphatic tetraamine, such as an alkylene tetraamine, or a salt thereof; an aliphatic pentaamine, such as an alkylene pentaamine, or a salt thereof; and an aliphatic ether diamine, such as an alkylene ether diamine, or a salt thereof. As the aqueous solvent, the solvent described for the step B may be used.

The concentration of the cross-linking agent in the water-resistant treatment liquid is preferably from 1 mass % to 50 mass %, more preferably from 5 mass % to 30 mass %. When the polarizer is brought into contact with the water-resistant treatment liquid, an organic dye in the polarizer is cross-linked through the cross-linking agent. The cross-linking provides a polarizer excellent in water resistance and mechanical strength.

The thickness of the iodine-based polarizer is preferably 15 µm or less, more preferably 13 µm or less, still more preferably 10 µm or less, particularly preferably 8 µm or less. The lower limit of the thickness of the iodine-based polarizer is 2 µm in one embodiment, and is 3 µm in another embodiment. The thickness of the lyotropic liquid crystal polarizer is preferably 1,000 nm or less, more preferably 700 nm or less, particularly preferably 500 nm or less. The lower limit of the thickness of the lyotropic liquid crystal polarizer is preferably 100 nm, more preferably 200 nm, particularly preferably 300 nm. When the thickness of the polarizer falls within such range, the projection light can be satisfactorily discharged from the housing, and the incidence (passing) of the sunlight into the housing can be suppressed.

The polarizer preferably shows absorption dichroism at any wavelength in the wavelength range of from 380 nm to 780 nm. The single layer transmittance of the polarizer is preferably from 35.0% to 50.0%, more preferably from 40.0% to 45.0%.

The polarization degree of the polarizer is 88% or more, and is preferably 89% or more, more preferably 90% or more.

C-2. Retardation Layers

As described above, the retardation layers each have a function of converting linearly polarized light into circularly polarized light or elliptically polarized light, or a function of converting circularly polarized light or elliptically polarized light into linearly polarized light. The refractive index characteristic of each of the retardation layers typically shows a relationship of $nx>ny$. As described above, the in-plane retardation Re(550) of each of the retardation layers is from 100 nm to 200 nm, preferably from 110 nm to 170 nm, more preferably from 130 nm to 150 nm. When the in-plane retardation falls within such range as described above, retardation films each having appropriate elliptical polarization performance can be obtained with excellent productivity and at reasonable cost. As a result, a head-up display apparatus capable of simultaneously satisfying concealability for its inside and display brightness can be obtained with excellent productivity and at reasonable cost.

The retardation layer shows any appropriate refractive index ellipsoid as long as the layer has the relationship of $nx>ny$. The refractive index ellipsoid of the retardation layer preferably shows a relationship of $nx>ny \geq nz$. The Nz coefficient of the retardation layer is preferably from 1 to 2, more preferably from 1 to 1.5, still more preferably from 1 to 1.3. The Nz coefficient is calculated from the expression "$Rth(\lambda)/Re(\lambda)$". The $Re(\lambda)$ is as described above. The term "$Rth(\lambda)$" refers to the thickness direction retardation of a film measured at 23° C. with light having a wavelength of $\lambda$ nm. When the thickness of the film is represented by d (nm), the $Rth(\lambda)$ is determined from the expression "$Rth=(nx-nz) \times d$" where "nz" represents the refractive index of the film in its thickness direction.

The polarizer and the retardation layer are laminated so that the absorption axis of the polarizer and the slow axis of the retardation layer form a predetermined angle. An angle formed between the absorption axis of the polarizer and the slow axis of the retardation layer is preferably from 35° to 55°, more preferably from 38° to 52°, still more preferably from 40° to 50°, particularly preferably from 42° to 48°, further particularly preferably around 45°. When the first retardation layer is arranged on an output side with respect to its corresponding polarizer (side opposite to the display cell) so as to satisfy such axial relationship, and the second retardation layer is arranged on a side closer to the inside of the housing with respect to its corresponding polarizer (side opposite to the cover member) so as to satisfy such axial relationship, a head-up display apparatus capable of simultaneously satisfying concealability for its inside and display brightness can be achieved.

The retardation layer includes any appropriate retardation film capable of satisfying such optical characteristics as described above. Typical examples of a resin for forming the retardation film include a cyclic olefin-based resin, a polycarbonate-based resin, a cellulose-based resin, a polyester-based resin, a polyvinyl alcohol-based resin, a polyamide-based resin, a polyimide-based resin, a polyether-based resin, a polystyrene-based resin, and an acrylic resin. When the retardation layer includes a resin film showing a reverse wavelength dispersion characteristic, the polycarbonate-based resin may be suitably used, and when the retardation layer includes a resin film showing a flat wavelength dispersion characteristic, the cyclic olefin-based resin may be suitably used.

The cyclic olefin-based resin is a collective term for resins each obtained by polymerizing a cyclic olefin as a polymerization unit, and examples thereof include resins described in, for example, JP 01-240517 A, JP 03-14882 A, and JP 03-122137 A. Specific examples thereof include a ring-opening (co)polymer of a cyclic olefin, an addition polymer of a cyclic olefin, and a copolymer (typically a random copolymer) of a cyclic olefin and an α-olefin, such as ethylene or propylene, and graft modified products obtained by modifying those polymers with an unsaturated carboxylic acid or a derivative thereof, and hydrogenated products thereof.

As the polycarbonate resin, any appropriate polycarbonate resin may be used as long as the effect of the present invention is obtained. The polycarbonate resin preferably contains: a structural unit derived from a fluorene-based dihydroxy compound; a structural unit derived from an isosorbide-based dihydroxy compound; and a structural unit derived from at least one dihydroxy compound selected from the group consisting of an alicyclic diol, an alicyclic dimethanol, di-, tri-, or polyethylene glycol, and an alkylene glycol or spiroglycol. The polycarbonate resin more preferably contains: a structural unit derived from a fluorene-based dihydroxy compound; a structural unit derived from an isosorbide-based dihydroxy compound; and a structural unit derived from an alicyclic dimethanol and/or a structural unit derived from di-, tri-, or polyethylene glycol. The polycarbonate resin still more preferably contains: a structural unit derived from a fluorene-based dihydroxy compound; a structural unit derived from an isosorbide-based dihydroxy compound; and a structural unit derived from di-, tri-, or polyethylene glycol. The polycarbonate resin may contain a structural unit derived from any other dihydroxy compound as required. Details of the polycarbonate resin that may be suitably used in the present invention are described in, for example, JP 2014-10291 A and JP 2014-26266 A, the descriptions of which are incorporated herein by reference.

Specific examples of the cellulose-based resin include cellulose (di or tri)acetate, cellulose propionate, cellulose butyrate, cellulose acetate propionate, cellulose acetate butyrate, cellulose acetate phthalate, and cellulose phthalate.

The retardation layer (retardation film) is typically produced by stretching a resin film formed from any such resin as described above in at least one direction.

Any appropriate method may be adopted as a method of forming the resin film. Examples thereof include a melt extrusion method (e.g., a T-die molding method), a cast coating method (e.g., a casting method), a calendar molding method, a hot press method, a co-extrusion method, a co-melting method, multilayer extrusion, and an inflation molding method. Of those, a T-die molding method, a casting method, and an inflation molding method are preferably used.

The thickness of the resin film (upstretched film) may be set to any appropriate value depending on, for example, the desired optical characteristics and stretching conditions to be described later. The thickness is preferably from 50 μm to 300 μm, more preferably from 80 μm to 250 μm.

Any appropriate stretching method and stretching conditions (e.g., a stretching temperature, a stretching ratio, and a stretching direction) may be adopted for the stretching. Specifically, one kind of various stretching methods, such as free-end stretching, fixed-end stretching, free-end shrinkage, and fixed-end shrinkage, may be employed alone, or two or more kinds thereof may be employed simultaneously or sequentially. With regard to the stretching direction, the stretching may be performed in various directions or dimensions, such as a horizontal direction, a vertical direction, a thickness direction, and a diagonal direction. The temperature at which the stretching is performed preferably falls within the range of the glass transition temperature (Tg) of the resin film ±20° C.

A retardation film (consequently a retardation layer) having the desired optical characteristics (e.g., a refractive index ellipsoid, an in-plane retardation, and an Nz coefficient) can be obtained by appropriately selecting the stretching method and stretching conditions.

In one embodiment, the retardation layer is produced by subjecting a resin film to uniaxial stretching or fixed-end uniaxial stretching. A specific example of the uniaxial stretching is a method involving stretching the resin film in its lengthwise direction (longitudinal direction) while running the resin film in its elongate direction. Another specific example of the uniaxial stretching is a method involving stretching the resin film in its lateral direction using a tenter. The stretching ratio is preferably from 10% to 500%.

In another embodiment, the retardation layer is produced by continuously subjecting a resin film having an elongate shape to oblique stretching in the direction of an angle θ with respect to its elongate direction. When the oblique stretching is adopted, a stretched film having an elongate shape and having an alignment angle that is an angle θ with respect to the elongate direction of the film is obtained, and for example, its lamination with the polarizer can be performed by a roll-to-roll process. As a result, the manufacturing process can be simplified. The angle θ corresponds to such angle formed between the absorption axis of the polarizer and the slow axis of the retardation layer as described above.

As a stretching machine to be used for the oblique stretching, for example, there is given a tenter stretching machine capable of applying feeding forces, or tensile forces or take-up forces, having different speeds on left and right sides in a lateral direction and/or a longitudinal direction. Examples of the tenter stretching machine include a lateral uniaxial stretching machine and a simultaneous biaxial stretching machine, and any appropriate stretching machine may be used as long as the resin film having an elongate shape can be continuously subjected to the oblique stretching.

As a method for the oblique stretching, there are given, for example, methods described in JP 50-83482 A, JP 02-113920 A, JP 03-182701 A, JP 2000-9912 A, JP 2002-86554 A, JP 2002-22944 A, and the like.

The thickness of the stretched film (consequently the retardation layer) is preferably from 20 pinto 80 μm, more preferably from 30 μm to 60 μm.

C-3. Substrate

The substrate is an optional constituent of the polarizing plate with a retardation layer, and is arranged as required. The substrate includes any appropriate film that may be used as a protective film for the polarizer. As a material serving as a main component of the film, there are specifically given, for example, cellulose-based resins, such as triacetylcellulose (TAC), and transparent resins, such as polyester-based, polyvinyl alcohol-based, polycarbonate-based, polyamide-based, polyimide-based, polyether sulfone-based, polysulfone-based, polystyrene-based, polynorbornene-based, polyolefin-based, cyclic olefin-based, (meth)acrylic, and acetate-based resins. There are also given, for example, thermosetting resins or UV-curable resins, such as (meth) acrylic, urethane-based, (meth)acrylic urethane-based, epoxy-based, and silicone-based resins. There are also given, for example, glassy polymers, such as a siloxane-based polymer. In addition, a polymer film described in JP 2001-343529 A (WO 01/37007 A1) may be used. For example, a resin composition containing a thermoplastic resin having a substituted or unsubstituted imide group on a side chain thereof, and a thermoplastic resin having a substituted or unsubstituted phenyl group and a nitrile group on side chains thereof may be used as a material for the film, and the composition is, for example, a resin composition containing an alternating copolymer formed of isobutene and N-methylmaleimide, and an acrylonitrile-styrene copolymer. The polymer film may be, for example, an extrudate of the resin composition. The (meth)acrylic resin or the cyclic olefin-based resin may be preferably used.

The glass transition temperature (Tg) of the (meth)acrylic resin is preferably 115° C. or more, more preferably 120° C. or more, still more preferably 125° C. or more, particularly preferably 130° C. or more. This is because the resin may be excellent in durability. Although the upper limit value of the Tg of the (meth)acrylic resin is not particularly limited, the upper limit is preferably 170° C. or less from the viewpoint of, for example, its formability.

Any appropriate (meth)acrylic resin may be adopted as the (meth)acrylic resin to the extent that the effects of the present invention are not impaired. Examples thereof include poly(meth)acrylic acid esters, such as polymethyl methacrylate, a methyl methacrylate-(meth)acrylic acid copolymer, a methyl methacrylate-(meth)acrylic acid ester copolymer, a methyl methacrylate-acrylic acid ester-(meth) acrylic acid copolymer, a methyl (meth)acrylate-styrene copolymer (e.g., an MS resin), and a polymer having an alicyclic hydrocarbon group (e.g., a methyl methacrylate-cyclohexyl methacrylate copolymer or a methyl methacrylate-norbornyl (meth)acrylate copolymer). Of those, a poly-$C_{1-5}$ alkyl (meth)acrylate, such as polymethyl (meth) acrylate, is preferred. Of those, a methyl methacrylate-based resin containing methyl methacrylate as a main component (from 50 wt % to 100 wt %, preferably from 70 wt % to 100 wt %) is more preferred.

Specific examples of the (meth)acrylic resin include: ACRYPET VH and ACRYPET VRL20A manufactured by Mitsubishi Rayon Co., Ltd.; a (meth)acrylic resin described in JP 2004-70296 A, the resin having a ring structure in a molecule thereof; and a high-Tg (meth)acrylic resin obtained by intramolecular cross-linking or an intramolecular cyclization reaction.

A (meth)acrylic resin having a lactone ring structure is particularly preferred as the (meth)acrylic resin because the resin has high heat resistance, high transparency, and high mechanical strength.

Examples of the (meth)acrylic resin having a lactone ring structure include (meth)acrylic resins each having a lactone ring structure described in JP 2000-230016 A, JP 2001-151814 A, JP 2002-120326 A, JP 2002-254544 A, and JP 2005-146084 A.

The (meth)acrylic resin having a lactone ring structure has a mass-average molecular weight (sometimes referred to as weight-average molecular weight) of preferably from 1,000 to 2,000,000, more preferably from 5,000 to 1,000,000, still more preferably from 10,000 to 500,000, particularly preferably from 50,000 to 500,000.

The glass transition temperature (Tg) of the (meth)acrylic resin having a lactone ring structure is preferably 115° C. or more, more preferably 125° C. or more, still more preferably 130° C. or more, particularly preferably 135° C. or more, most preferably 140° C. or more. This is because the resin may be excellent in durability. Although the upper limit value of the Tg of the (meth)acrylic resin having a lactone ring structure is not particularly limited, the upper limit value is preferably 170° C. or less from the viewpoint of, for example, its formability.

The term "(meth)acrylic" as used herein refers to acrylic and/or methacrylic.

The cyclic olefin-based resin is as described for the retardation films in the section C-2.

When the lyotropic liquid crystal polarizer is adopted, the substrate having applied thereto the coating liquid containing the aromatic disazo compound may be used as it is as the substrate, or the following may be performed: the substrate is peeled, and such protective film as described above is bonded to the peeling surface.

It is preferred that the substrate be optically isotropic. The phrase "be optically isotropic" as used herein means that the in-plane retardation Re(550) of the substrate is from 0 nm to 10 nm, and the thickness direction retardation Rth(550) thereof is from −10 nm to +10 nm.

The thickness of the substrate is preferably from 20 μm to 80 μm, more preferably from 30 μm to 60 μm.

C-4. Others

The polarizing plate with a retardation layer may further have a hard coat layer and/or an antiblocking layer on the opposite side of the substrate to the polarizer as required. The hard coat layer is described in detail in, for example, JP 2007-171943 A. The antiblocking layer is described in detail in, for example, JP 2015-115171A, JP 2015-141674 A, JP 2015-120870 A, and JP 2015-005272 A. The descriptions of those publications are incorporated herein by reference.

The polarizer and the retardation layer are bonded to each other via any appropriate adhesion layer. When the iodine-based polarizer is used, the polarizer and the substrate are bonded to each other via any appropriate adhesion layer. The adhesion layer may be a pressure-sensitive adhesive layer, or may be an adhesive layer. A pressure-sensitive adhesive forming the pressure-sensitive adhesive layer may typically be an acrylic pressure-sensitive adhesive. An adhesive forming the adhesive layer may typically be an energy ray-curable adhesive.

EXAMPLES

Now, the present invention is specifically described byway of Examples. However, the present invention is by no means limited to these Examples. Evaluation items in Examples are as described below.

(1) Concealability for Inside

A fluorescent lamp (manufactured by Gentos Co., Ltd., "DK-S70CWH") was arranged at a position distant from an end of the case (housing) of each of head-up display apparatus-corresponding products obtained in Examples and Comparative Examples by 100 mm in a lateral direction and by 400 mm in an upward direction, and the reflection brightness of the bottom of the housing was measured with a brightness meter (manufactured by Topcon Corporation, "SR-UL1") under a state in which the power source of the liquid crystal display apparatus of the corresponding product was turned off. Further, the viewability of the inside of the housing was visually confirmed, and was evaluated by the following criteria.

○: The liquid crystal display apparatus in the housing could not be viewed.

x: The liquid crystal display apparatus in the housing was clearly viewed.

(2) Display Brightness

The display brightness of the liquid crystal display apparatus of each of the head-up display apparatus-corresponding products obtained in Examples and Comparative Examples was measured with a brightness meter (manufactured by Topcon Corporation, "SR-UL1").

Example 1

1. Synthesis of Organic Dye (Aromatic Disazo Compound) 4-Nitroaniline and 8-amino-2-naphthalenesulfonic acid were subjected to diazotization and a coupling reaction by an ordinary method (method described in "Theoretical Production Dye Chemistry Fifth Edition" written by Yutaka Hosoda and published by Gihodo on Jul. 15, 1968, p. 135 to 152) to provide a monoazo compound. The resultant monoazo compound was diazotized by the ordinary method, and was further subjected to a coupling reaction with lithium 1-amino-8-naphthol-2,4-disulfonate to provide a crude product. The crude product was salted out with lithium chloride to provide an aromatic disazo compound represented by the following formula (4).

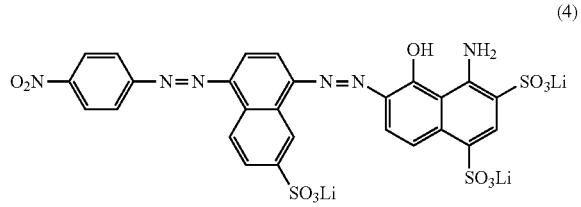

(4)

2. Production of Polarizing Plate

A norbornene-based resin film (manufactured by Zeon Corporation: product name: "ZEONOR ZF14-100") was prepared as a substrate, and the surface of the film was subjected to rubbing treatment and hydrophilic treatment (corona treatment). The aromatic disazo compound represented by the formula (4) was dissolved in ion-exchanged water to prepare a coating liquid having a concentration of 4 wt %. The coating liquid was applied to the surface of the substrate subjected to the rubbing treatment and the hydrophilic treatment with a bar coater (manufactured by Buschman: product name: "Mayer rod HS4"), and was naturally dried in a thermostatic chamber at 23° C. to form a dried coating film (polarizer) on the surface of the substrate. The thickness of the polarizer was 300 nm.

Subsequently, the laminate having the configuration "substrate/polarizer" was immersed in a water-resistant treatment liquid for 2 seconds. An aqueous solution containing 1,3-propanediamine hydrochloride (manufactured by Tokyo Chemical Industry Co., Ltd.), 1,2-ethylenediamine hydrochloride (manufactured by Tokyo Chemical Industry Co., Ltd.), and bis(hexamethylene)triamine (manufactured by Tokyo Chemical Industry Co., Ltd.) at a mass ratio of 55:15:30 was used as the water-resistant treatment liquid. The laminate having the configuration "substrate/polarizer", which had been removed from the water-resistant treatment liquid, was washed with water and dried to provide a polarizer having imparted thereto water resistance (laminate having the configuration "substrate/polarizer").

3. Retardation Film Forming Retardation Layer

"ARTON 4RJT1403" (manufactured by JSR Corporation) was used as a retardation film forming a retardation layer.

4. Production of Polarizing Plate with Retardation Layer

The laminate having the configuration "substrate/polarizer" and the retardation film were bonded to each other so that the polarizer and the retardation film faced each other. An acrylic pressure-sensitive adhesive (manufactured by Nitto Denko Corporation, product name: "CS9861UA") was used in the bonding. In addition, the bonding was performed so that the absorption axis of the polarizer and the slow axis of the retardation film formed an angle of 45°. Thus, a polarizing plate with a retardation layer having the configuration "substrate/polarizer/retardation film (retardation layer)" was obtained. The two polarizing plates with retardation layers were prepared, and were used as a first polarizing plate with a retardation layer and a second polarizing plate with a retardation layer.

5. Production of Laminate Having Configuration "Second Polarizing Plate with Retardation Layer/Cover Member"

A polycarbonate-based resin sheet having a thickness of 300 μm (manufactured by Mitsubishi Gas Chemical Company, Inc.: product name: "MRF08U") was used as a cover member. The cover member and the second polarizing plate with a retardation layer were bonded to each other via an acrylic pressure-sensitive adhesive (manufactured by Nitta Denko Corporation: product name: "CS9862UA") so that the cover member and the substrate faced each other. Thus, a laminate having the configuration "polarizing plate with a retardation layer/cover member" was produced.

6. Production of Head-Up Display Apparatus-Corresponding Product

A case having a size measuring 200 mm by 150 mm by 200 mm, the case having an open top, was produced by using carbon-containing conductive plastic cardboard (manufactured by Yamakoh Co., Ltd.).

Meanwhile, a liquid crystal display apparatus with a backlight was taken out of a portable information terminal (manufactured by Apple Inc., "i-pad mini"), and its polarizing plate on a viewer side was removed. The first polarizing plate with a retardation layer obtained in the foregoing was bonded to the surface from which the polarizing plate had been removed. The liquid crystal display apparatus having bonded thereto the first polarizing plate with a retardation layer was placed in the case.

Next, the laminate having the configuration "second polarizing plate with a retardation layer/cover member", which had been obtained in the foregoing, was used to cover the opening portion of the case so that the cover member faced the outside. At this time, the first polarizing plate with a retardation layer and the second polarizing plate with a retardation layer were arranged so that the absorption axes of their respective polarizers were parallel to each other, and the slow axes of their respective retardation layers were perpendicular to each other.

Thus, a head-up display apparatus-corresponding product was produced. The resultant head-up display apparatus-corresponding product was subjected to the evaluations (1) and (2). The results are shown in Table 1.

Example 2

A head-up display apparatus-corresponding product was produced in the same manner as in Example 1 except that both the retardation values of the first retardation layer and the second retardation layer were set to 110 nm. The resultant head-up display apparatus-corresponding product was subjected to the same evaluations as those of Example 1. The results are shown in Table 1.

Example 3

A head-up display apparatus-corresponding product was produced in the same manner as in Example 1 except that both the retardation values of the first retardation layer and the second retardation layer were set to 190 nm. The resultant head-up display apparatus-corresponding product was subjected to the same evaluations as those of Example 1. The results are shown in Table 1.

Example 4

A head-up display apparatus-corresponding product was produced in the same manner as in Example 1 except that the retardation value of the first retardation layer was set to 120 nm, and the retardation value of the second retardation layer was set to 190 nm. The resultant head-up display apparatus-corresponding product was subjected to the same evaluations as those of Example 1. The results are shown in Table 1.

Comparative Example 1

A head-up display apparatus-corresponding product was produced in the same manner as in Example 1 except that the first retardation layer was not arranged. The resultant head-up display apparatus-corresponding product was subjected to the same evaluations as those of Example 1. The results are shown in Table 1.

Comparative Example 2

A head-up display apparatus-corresponding product was produced in the same manner as in Example 1 except that none of the first retardation layer and the second retardation layer was arranged. The resultant head-up display apparatus-corresponding product was subjected to the same evaluations as those of Example 1. The results are shown in Table 1.

TABLE 1

| | Retardation layer | Reflection brightness | Viewability | Display brightness |
|---|---|---|---|---|
| Example 1 | 140 nm × 2 layers | 4 cd/m² | ○ | 350 cd/m² |
| Example 2 | 110 nm × 2 layers | 6 cd/m² | ○ | 347 cd/m² |
| Example 3 | 190 nm × 2 layers | 5 cd/m² | ○ | 345 cd/m² |
| Example 4 | 120 nm × 1 layer 190 nm × 1 layer | 7 cd/m² | ○ | 290 cd/m² |
| Comparative Example 1 | 140 nm × 1 layer Cover side | 4 cd/m² | ○ | 170 cd/m² |
| Comparative Example 2 | None | 11 cd/m² | x | 348 cd/m² |

(Concealability for inside: Reflection brightness, Viewability)

As is apparent from Table 1, it is found that each of the head-up display apparatus of Examples simultaneously satisfies concealability for its inside and display brightness.

INDUSTRIAL APPLICABILITY

The head-up display apparatus according to the embodiment of the present invention may be suitably used in a vehicle including a windshield (typically an automobile).

REFERENCE SIGNS LIST

10 display unit
11 display cell
12 first polarizing plate with retardation layer
20 reflector
30 housing
40 cover member
50 second polarizing plate with retardation layer
100 head-up display apparatus
101 head-up display apparatus

The invention claimed is:

1. A head-up display apparatus, comprising:
a display unit, which includes a display cell and a first polarizing plate with a retardation layer arranged on an output side of the display cell, the first polarizing plate with a retardation layer including a polarizer and a first retardation layer in the stated order from a display cell side, and which is configured to output projection light;
at least one reflector configured to reflect the projection light;
a housing, which has an opening portion, and which is configured to store the display unit and the reflector therein;
a cover member configured to cover the opening portion; and
a second polarizing plate with a retardation layer, which is arranged on a housing inner side of the cover member, and which includes a polarizer and a second retardation layer in the stated order from a cover member side,
wherein the first retardation layer and the second retardation layer each have an in-plane retardation Re(550) of from 100 nm to 200 nm.

2. The head-up display apparatus according to claim 1, wherein the polarizer contains an aromatic disazo compound represented by the following formula (1):

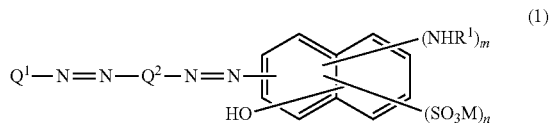

in the formula (1), $Q^1$ represents a substituted or unsubstituted aryl group, $Q^2$ represents a substituted or unsubstituted arylene group, $R^1$s each independently represent a hydrogen atom, a substituted or unsubstituted alkyl group, a substituted or unsubstituted acetyl group, a substituted or unsubstituted benzoyl group, or a substituted or unsubstituted phenyl group, M represents a counterion, "m" represents an integer of from 0 to 2, and "n" represents an integer of from 0 to 6, provided that at least one of "m" or "n" does not represent 0, a relationship of 1≤m+n≤6 is satisfied, and when "m" represents 2, the respective $R^1$s may be identical to or different from each other.

3. The head-up display apparatus according to claim 1, wherein the polarizers each have a thickness of from 100 nm to 1,000 nm.

4. The head-up display apparatus according to claim 1, wherein the head-up display apparatus is configured so that an angle of reflection of the projection light output from the housing through the opening portion with respect to a windshield is from 10° to 50°.

* * * * *